US005746810A

United States Patent [19]

Suzuki

[11] Patent Number: 5,746,810
[45] Date of Patent: May 5, 1998

[54] AQUEOUS EMULSION OF ALKYLALKOXYSILANE, PROCESS FOR THE PRODUCTION THEREOF, AND USE THEREOF

[75] Inventor: Takehiro Suzuki, Tokyo, Japan

[73] Assignee: Toyo Ink Manufacturing Co., Ltd., Tokyo, Japan

[21] Appl. No.: 646,496

[22] Filed: May 8, 1996

[51] Int. Cl.⁶ .............................. C09K 3/18; C09D 5/00; B01J 13/00
[52] U.S. Cl. .......................... 106/2; 106/287.14; 252/312
[58] Field of Search .............................. 252/312, 315.2; 106/2, 287.14; 405/270

[56] References Cited

U.S. PATENT DOCUMENTS

| 4,518,727 | 5/1985 | Traver | 106/287.14 X |
| 4,648,904 | 3/1987 | DePasquale et al. | 106/2 |
| 4,874,547 | 10/1989 | Narula | 252/312 |
| 4,877,654 | 10/1989 | Wilson | 106/2 X |
| 4,990,377 | 2/1991 | Wilson | 106/2 X |
| 5,091,002 | 2/1992 | Schamberg et al. | 106/287 |
| 5,226,954 | 7/1993 | Suzuki | 106/2 |
| 5,531,812 | 7/1996 | Montigny et al. | 106/2 |

FOREIGN PATENT DOCUMENTS

| 0 392 253 | 10/1990 | European Pat. Off. . |
| 0 616 989 | 9/1994 | European Pat. Off. . |

*Primary Examiner*—Richard D. Lovering
*Attorney, Agent, or Firm*—Wenderoth, Lind & Ponack

[57] ABSTRACT

An aqueous emulsion of alkylalkoxysilane which has a stable emulsion state for a long period of time and is useful as an infiltrative preventer of water absorption into a porous inorganic construction material, the emulsion containing an alkylalkoxysilane, water and an emulsifier, wherein droplets of the alkylalkoxysilane in the water has a diameter in the range of from 0.5 to 10 μm, and a process for the production of an aqueous alkylalkoxysilane emulsion, which comprises emulsifying and dispersing an alkylalkoxysilane, water and an emulsifier under conditions sufficient to form an emulsion in which droplets of the alkylalkoxysilane in the water has a diameter in the range of from 0.5 to 10 μm.

11 Claims, No Drawings

AQUEOUS EMULSION OF ALKYLALKOXYSILANE, PROCESS FOR THE PRODUCTION THEREOF, AND USE THEREOF

BACKGROUND OF THE INVENTION

1. Field of the Invention

The present invention relates to an aqueous emulsion of alkylalkoxysilane which has a stable emulsion state for a long period of time and is useful as an infiltrative preventer of water absorption into a porous inorganic construction material such as concrete.

2. Description of Related Art

It is well known that alkylalkoxysilane is useful as a water repellency agent or an infiltrative water-absorption preventer for porous inorganic construction materials such as concrete. An infiltrative water-absorption preventer is infiltrated into a surface layer of a porous inorganic construction material to form a hydrophobic layer, and as a result, the hydrophobic layer protects the porous inorganic construction material by preventing the infiltration of water, salts, etc. The infiltrative water-absorption preventer is therefore recently more highly valued than a water repellency agent which simply provides a construction material with water repellency. There is therefore increasingly strong demand for an alkylalkoxysilane which has excellent infiltrativity and can form a strong hydrophobic layer by a chemical reaction. It has been general practice to dilute alkylalkoxysilanes with various organic solvents. However, field of the use thereof has been limited due to the properties of organic solvents such as toxicity, volatility and ignitability.

For example, when used as a solvent, even isopropyl alcohol of which the toxicity is relatively low limits the infiltration of alkylalkoxysilane into a substrate (construction material) due to its high evaporation rate. There is another problem in that organic solvents inhibit the application of alkylalkoxysilane to a wet surface. Moreover, a silane-based absorptive water-absorption preventer containing no organic solvent is required in view of environmental problems. For overcoming the above problems, the following means have been proposed and commercialized.

1) Alkylalkoxysilane is directly applied.
2) Alkylalkoxysilane is hydrolyzed and applied in the form of an aqueous solution.
3) Alkylalkoxysilane is applied in the form of a water-based dispersion.

However, the above means still have the following new problems.

i) Although having a high flash point and low toxicity, alkylalkoxysilane comes under dangerous substances under the fire law. It therefore cannot be said that the transportation and use of alkylalkoxysilane itself are any improvement in view of environmental problems. Further, it is difficult to apply the alkylalkoxysilane to a wet substrate surface.

ii) When alkylalkoxysilane is hydrolyzed, silane itself is liable to undergo condensation. Solubilized alkylalkoxysilane therefore shows an extremely decreased pot life. It is therefore necessary to solubilize alkylalkoxysilane at a site where it is used, and it is required to consume all the solubilized alkylalkoxysilane at the site, which requires complex works and is not economical.

iii) Alkylalkoxysilane is liable to undergo hydrolysis and subsequent condensation, and it is therefore difficult to maintain alkylalkoxysilane stably in water. That is, the pot life thereof is not satisfactory. Further, due to the use of a dispersion stabilizer, the alkylalkoxysilane after applied to a substrate is poor in the capability of preventing water absorption.

If the problems concerning the pot life and the capability of preventing water absorption can be overcome, the above means (3) of applying alkylalkoxysilane in the form of an aqueous dispersion is optimum, and some methods therefor have been studied.

JP-B-3-13195 discloses a method of emulsifying a hydrolyzable organic silicon compound such as alkylalkoxysilane in the presence of a nonionic emulsifier having an HLB value of 4 to 15. However, an emulsion in the presence of a nonionic emulsifier alone is liable to be separated into two phases, and it is difficult to obtain a stable aqueous emulsion by a simple method. In emulsifying some silanes, it is difficult to select optimum conditions concerning the HLB value and the amount of an emulsifier. Further, the infiltrativity of alkylalkoxysilane differs depending upon the type of the emulsifier, a solid or a liquid, even if the HLB value of the emulsifier is the same. If a balance between water prevention and stability, or the infiltrativity is taken into consideration, the emulsifier that can be used is limited. Further, a relatively large amount of the nonionic emulsifier is required, which deteriorates the water-absorption prevention performance of alkylalkoxysilane and water repellency of the alkylalkoxysilane on a surface.

JP-B-7-5400 discloses an aqueous organic silicon-containing composition prepared by emulsifying alkylalkoxysilane in an aqueous medium in the presence of a nonionic emulsifier and an anionic emulsifier (the amount of the anionic emulsifier is based on the total amount of the nonionic emulsifier and the anionic emulsifier is 0.01 to 20% by weight). The above composition is not only excellent in the stability as performance of an infiltrative water-absorption preventer for a construction material but also stable for more than six months without causing phase separation. Further, the above composition can be easily prepared since it is not necessary to strictly select the conditions of the emulsification of alkylalkoxysilane.

However, the above composition still has the following problems. When an emulsion prepared by simply emulsifying alkylalkoxysilane is stored at room temperature for more than one year, the emulsion is separated into two phases and in some cases, it is difficult to re-emulsify the two-phase composition by simply shaking it. Silane undergoes condensation due to a change in time and does not infiltrate a construction material such as concrete, and the applied surface shows a wet color in some cases. The higher the temperature at which the above composition is stored at, the quicker the above tendency takes place. Further, the storage stability of the above composition varies.

SUMMARY OF THE INVENTION

It is an object of the present invention to provide an aqueous emulsion of alkylalkoxysilane which has a stable emulsion state for a long period of time and is useful as an infiltrative preventer of water absorption into a porous inorganic construction material (to be sometimes referred to as "substrate" hereinafter) such as concrete.

According to the present invention, there is provided an aqueous alkylalkoxysilane emulsion containing an alkylalkoxysilane, water and an emulsifier, wherein droplets of the alkylalkoxysilane in the water has a diameter in the range of 0.5 to 10 μm.

According to the present invention, further, there is provided a process for the production of an aqueous alkylalkoxysilane emulsion, which comprises emulsifying and dispersing an alkylalkoxysilane, water and an emulsifier under conditions sufficient to form an emulsion in which droplets of the alkylalkoxysilane in the water has a diameter in the range of 0.5 to 10 μm.

According to the present invention, further, there is provided an infiltrative water-absorption preventor for a porous inorganic construction material, which contains the above aqueous alkylalkoxysilane emulsion as an active ingredient.

DETAILED DESCRIPTION OF THE INVENTION

In the present invention, the droplets of liquid alkylalkoxysilane in water is measured for a diameter as follows. An emulsion is sandwiched between a slide and a glass cover without including bubbles, its photograph is taken through an optical microscope, and droplets were compared with a scale.

When the droplets of liquid alkylalkoxysilane in water has a diameter of 0.5 to 10 μm, the droplets are stably dispersed, and even after more than 1 year, the emulsion is simply separated into an opaque layer of a silane-concentrated emulsion and a colorless transparent layer of water, so that an emulsion is easily formed by re-emulsification. Further, droplets of silane molecules are formed, and most of the silane molecules, i.e., silane molecules inside each droplet, are out of contact with water, so that most of the silane molecules are free from being hydrolyzed.

When droplets having a diameter of more than 10 μm are present, droplets themselves are liable to collide with one another to form droplets having a larger size, and silane and water are separated. As a result, no emulsion can be formed by re-emulsification.

However, it is not meant that droplets having smaller diameters are preferred. When the diameter of the droplets is too small, the contact possibility between alkoxysilyl group and water increases, and the alkylalkoxysilane molecules are easily hydrolyzed, and the hydrolysis forms ethanol. The emulsion is accordingly broken. As a result, in some cases, no emulsion can be formed by re-emulsification, the applied surface of concrete shows a wet color, gelation takes place or the pot life is decreased.

Even in the emulsion having a silane concentration effective for impregnating concrete with the emulsion, i.e., 5 to 70% by weight, the diameter of silane droplets can be decreased to 0.5 μm by properly adjusting the amount of the emulsifiers the and treating conditions of an emulsifying and dispersing apparatus.

The alkylalkoxysilane used in the present invention comprises at least one alkyl group having 6 to 20 carbon atoms, at least one alkoxy group selected from methoxy, ethoxy or propoxy group and a silicon atom, in which the alkyl group and the alkoxy group directly bond to the silicon atom. The alkoxy group is preferably an ethoxy group. Preferred is monoalkyltrialkoxysilane. Although not specially limited, examples of the alkylalkoxysilane include hexyltriethoxysilane, heptyltriethoxysilane, octyltriethoxysilane, nonyltriethoxysilane, decyltriethoxysilane, undecyltriethoxysilane, dodecyltriethoxysilane, tridecyltriethoxysilane, tetradecyltriethoxysilane, pentadecyltriethoxysilane, hexadecyltriethoxysilane, heptadecyltriethoxysilane, octadecyltriethoxysilane, nonadecyltriethoxysilane, eicosyltriethoxysilane, and mixtures of these.

When the number of carbon atoms of the alkyl group bonding to silicon is smaller than 6, the alkylalkoxysilane has high hydrolyzability and volatility, and part of the alkylalkoxysilane molecules therefore react on the substrate surface to delay the infiltration of the emulsion. Further, at the same time, unreacted silane components are liable to evaporate. As a result, the substrate surface is simply imparted with water repellency alone. When the number of carbon atoms of the alkyl group is greater than 20, the alkylalkoxysilane has a large molecular weight and the infiltration thereof is therefore poor.

When the alkoxy group is methoxy, undesirably, the alkylalkoxysilane is poor under alkaline conditions, and the alkylalkoxysilane is liable to undergo bonding or cross-linking on the substrate surface before it infiltrates the substrate. Further, the emulsion is poor in stability. When the alkoxy group has a carbon chain greater than propoxy, the alkylalkoxysilane is slower to bond to the substrate after it infiltrates the substrate since it is more stable, and as a result, undesirably, it requires an additional time before the alkylalkoxysilane exhibits its effect.

For densifying and reinforcing a porous inorganic construction material, the above alkylalkoxysilane may be used in combination with tetralkoxysilane or its condensation product in such an amount that does not affect the emulsion stability. For improving the alkylalkoxysilane in properties such as bonding and contacting properties to an overcoating material, the alkylalkoxysilane may be used in combination with an alkoxysilane having any one of amino, methacryloxyl, vinyl, epoxy or thiol group in such an amount that does not affect the emulsion stability.

The concentration of the alkylalkoxysilane in the emulsion is preferably 5 to 70% by weight. When the concentration of the alkylalkoxysilane is less than 5% by weight, it is difficult to impart concrete with sufficient performance of water absorption prevention by applying the emulsion once. Further, as the application of the emulsion is repeated, the infiltrativity of the alkylalkoxysilane into a porous inorganic construction material decreases. The dilute emulsion having an alkylalkoxysilane concentration of less than 5% by weight is therefore not suitable for use as a water-absorption preventer for a porous inorganic construction material. When the concentration of the alkylalkoxysilane in the emulsion exceeds 70% by weight, it is difficult to decrease the diameter of the alkylalkoxysilane in water to 0.5~10 μm, and the stability of the emulsion is also poor.

The emulsifier is not specially limited, and it includes an anionic emulsifier, a nonionic emulsifier, a cationic emulsifier and an amphoteric emulsifier.

The amount of the emulsifier based on the silane component is 0.1 to 50% by weight, preferably 0.1 to 5% by weight. When the amount of the emulsifier is less than 0.1% by weight, no stable emulsion is obtained. When it exceeds 50% by weight, no sufficient performance of water absorption prevention is obtained.

Although not specially limited, the anionic emulsifier includes fatty acid salt, alkyl sulfuric acid ester salt, alkylaryl sulfonic acid salt, alkylnaphthalene sulfonic acid salt, dialkyl sulfosuccinic acid salt, alkyl diaryl ether disulfonic acid salt, alkyl phosphoric acid ester or salt, alkylpolyoxyethylene ether sulfuric acid ester salt, alkylaryl polyoxyethylene ether sulfuric acid ester salt, naphthalene sulfonic acid formaline condensate, polyoxyethylene alkylphsophoric acid ester or salt, glycerol borate fatty acid ester or salt and polyoxyethylene glycerol borate fatty acid ester or salt.

Although not specially limited, the nonionic emulsifier includes polyoxyethylene alkyl ether, polyoxyethylene alkylaryl ether, a polyoxyethylene-oxypropylene block copolymer, sorbitan fatty acid ester, polyoxyethylene sorbitan fatty acid ester, polyoxyethylene sorbitol fatty acid ester, glycerin fatty acid ester, polyoxyethylene fatty acid ester, polyoxyethylenealkylamine, a fluorine-containing nonionic emulsifier and a silicone-containing nonionic emulsifier.

Although not specially limited, the cationic emulsifier includes alkylamine salt, quaternary ammonium salt, alkyl pyridinium salt and alkyl imidazolium salt.

Although not specially limited, the amphoteric emulsifier includes alkylbetaine, alkylamine oxide and phosphatidyl choline (also called lecithin).

The above emulsifiers may be used alone or in combination, and it is the most preferred to use an anionic emulsifier and a nonionic emulsifier in combination. When an anionic emulsifier and a nonionic emulsifier are used in combination, the amount of the total emulsifier amount necessary for emulsifying the alkylalkoxysilane can be decreased, and there is accordingly almost no adverse effect of the emulsifier on the water resistance. When an anionic emulsifier and a nonionic emulsifier are used in combination, the amount of the anionic emulsifier based on the total emulsifier amount is preferably 0.01 to 20% by weight. When one emulsifier is used alone, or when the amount of the anionic emulsifier exceeds 20% in the above case, it is likely to be difficult to produce a stable emulsion, and the emulsion is liable to undergo phase separation.

The aqueous alkylalkoxysilane emulsion of the present invention may contain additives such as a pH adjusting agent, an antiseptic agent, a mildew proofing agent, an antibacterial agent, a thickening agent, a water-based water repellency agent, an anti-foaming agent, an oil-soluble dye and a water-based colorant as required, so long as the additives do not affect the dispersibility of the alkylalkoxysilane and the performance thereof as an infiltrative water-absorption preventer.

The pH adjusting agent is added for preventing the hydrolysis of the alkoxy group by adjusting the pH of the emulsion to a 7 to 9.5 weak alkali side. The pH adjusting agent is selected from various alkali compounds and pH buffers. Examples of the alkali compounds include metal hydroxides such as sodium hydroxide and calcium hydroxide, and organic amines such as propylamine, isoamylamine, hexylamine, laurylamine and stearylamine.

The antiseptic agent prevents the decomposition of the emulsion, and the mildew proofing agent and the antibacterial agent prevent the propagation of mildew and bacteria on the emulsion-applied substrate surface. These agents can be used without any special limitation so long as they do not impair the stability of the emulsion. Examples of these agents include haloallylsulfone-containing, iodopropargyl-containing, N-haloalkylthio-containing, benzoimidazole-containing, nitrile-containing, pyridine-containing, 8-oxyquinoline-containing, benzothiazole-containing, isothiazoline-containing, organic tin-containing, phenol-containing, quaternary ammonium-containing, triazine-containing, thiadiazine-containing, anilide-containing, adamantane-containing, dithiocarbamate-containing, inorganic salt-containing, and brominated indanone-containing compounds. Of the above compounds, those compounds which are easily soluble in water can be used as an antiseptic agent, and those which are not easily soluble in water can be used as a mildew proofing agent or an antibacterial agent. The above compounds may be used alone or in combination.

The thickening agent improves the stability of the emulsion against phase separation. The thickening agent is not specially limited if it has no adverse effect on the stability of the silane and an emulsion-applied substrate surface. Examples of the thickening agent include water-soluble polymers such as modified polyacrylic acid, modified polyacrylic acid salt, polyacrylic acid, alkali salt of polyacrylic acid, alginic acid salt, alginic acid ester, polyvinyl alcohol, polyether, casein, mannan, starch, chitosan, carboxymethyl cellulose and methoxymethyl cellulose. These polymers may be used alone or in combination.

The water-based water repellency agent is used when the aqueous alkylalkoxysilane emulsion is applied to a porous inorganic construction material which the aqueous alkylalkoxysilane emulsion easily infiltrates so that the surface of the construction material is not provided with sufficient water repellency. The water-based water repellency agent is not specially limited so long as it has no adverse effect on the stability of the silane and the surface state of the emulsion-applied substrate. Examples of the water-based water repellency include a silicone-containing aqueous emulsion water repellency agent, a fluorine-containing aqueous emulsion water repellency agent and a zirconium-containing aqueous water repellency agent.

The aqueous alkylalkoxysilane emulsion of the present invention can be obtained by emulsifying the alkylalkoxysilane, water, the emulsifier and optionally, other additives with an emulsifying and dispersing machine under conditions sufficient to form an emulsion in which droplets of the alkylalkoxysilane in the water has a diameter in the range of from 0.5 to 10 μm. The diameter of the droplets can be adjusted by selecting an emulsifying and dispersing machine and adjusting emulsification conditions such as a stirring rate or an ejection pressure from a nozzle, an emulsification time, and the like. The emulsifying and dispersing machine can be preferably selected from emulsifying and dispersing machines suitable for low-viscosity emulsification such as a high-speed emulsifying and dispersing machine "T.K. homomixer", an ultrafine-particle emulsifying and dispersing machine "T.K. micromizer", an ultrahigh-pressure emulsifying and dispersing system "T.K. nanomizer" (all of these are supplied by Tokushu Kika Kogyo K. K.), a high-speed dispersing fine-particles-forming machine "ULTRATURRAX" supplied by IKA-MASCHINENBAU, "CLEARMIX" supplied by M. Technic, and a hydraulic ultrahigh-pressure homogenizer "Microfluidizer" supplied by Mizuho Kogyo K. K. When the alkylalkoxysilane, water, the emulsifier and optionally, other additives are treated with the above emulsifying and dispersing machine at a high rate or under high pressure, the temperature of the mixture increases in some cases, and the emulsifying power of the machine may decrease. It is therefore preferred to maintain the temperature of the mixture at a temperature of 50° C. or lower by cooling a container.

EXAMPLE 1

500 Grams of n-hexyltriethoxysilane, 2.0 g of polyoxyethylene (20 mol) stearyl ether, 0.02 g of sodium laurylsulfate, 2.0 g of a 1% sodium hydroxide aqueous solution, 0.5 g of 1,2-benzoisothiazolin-3-one, 2.0 g of 2-n-octyl-4-isothiazolin-3-one and 500 g of water were stirred with a homomixer at a rate of 10,000 rpm for 60 minutes, to give a white aqueous emulsion. The emulsion was observed through an optical microscope to show that silane droplets had a diameter of about 2 μm and that droplets having a diameter of more than 10 μm were absent.

EXAMPLE 2

A white aqueous emulsion was obtained in the same manner as in Example 1 except that the number of revolution of the homomixer was changed from 10,000 rpm to 5,000 rpm. The emulsion was observed through an optical microscope to show that silane droplets had a diameter of about 5 µm and that droplets having a diameter of more than 10 µm were absent.

EXAMPLE 3

A white aqueous emulsion was obtained in the same manner as in Example 1 except that the number of revolution of the homomixer was changed from 10,000 rpm to 3,000 rpm and that the stirring time was changed from 60 minutes to 90 minutes. The emulsion was observed through an optical microscope to show that silane droplets had a diameter of about 8 µm and that droplets having a diameter of more than 10 µm were absent.

EXAMPLE 4

A white aqueous emulsion was obtained in the same manner as in Example 2 except that the n-hexyltriethoxysilane was replaced with n-octyltriethoxysilane. The emulsion was observed through an optical microscope to show that silane droplets had a diameter of about 5 µm and that droplets having a diameter of more than 10 µm were absent.

EXAMPLE 5

500 Grams of n-hexyltriethoxysilane, 2.0 g of alkylphosphoric acid ester ("Newcol 1000FCP, supplied by Nippon Nyukazai K. K.), 5.0 g of a modified polyacrylic acid emulsion (SN thickener-A-850, supplied by SANNOPCO LIMITED), 0.5 g of 1,2-benzoisothiazolin-3-one, 2.0 g of 2-n-octyl-4-isothiazolin-3-one and 500 g of water were stirred with a homomixer at a rate of 5,000 rpm for 60 minutes, to give a white aqueous emulsion. The emulsion was observed through an optical microscope to show that silane droplets had a diameter of about 1 µm and that droplets having a diameter of more than 10 µm were absent.

EXAMPLE 6

500 Grams of n-hexyltriethoxysilane, 2.0 g of phosphatidyl choline, 2.0 g of a 1% sodium hydroxide aqueous solution, 0.5 g of 1,2-benzoisothiazolin-3-one, 2.0 g of 2-n-octyl-4-isothiazolin-3-one and 500 g of water were stirred with a homomixer at a rate of 5,000 rpm for 60 minutes, to give a white aqueous emulsion. The emulsion was observed through an optical microscope to show that silane droplets had a diameter of about 5 µm and that droplets having a diameter of more than 10 µm were absent.

EXAMPLE 7

100 Grams of a zirconium-containing water-based emulsion water repellency agent (ZIRCOPEL CA, supplied by Daiichi Kigenso K. K.) was mixed with 1,000 g of the emulsion obtained in Example 1, to give a white aqueous emulsion. The emulsion was observed through an optical microscope to show that silane droplets had a diameter of about 5 µm and that droplets having a diameter of more than 10 µm were absent.

Comparative Example 1

A white aqueous emulsion was obtained in the same manner as in Example 1 except that the amount of the polyoxyethylene stearyl ether was changed from 2.0 g to 100 g, that the amount of the sodium laurylsulfate was changed from 0.02 g to 1 g and the stirring time with a homomixer was changed from 60 minutes to 120 minutes. The emulsion was observed through an optical microscope to show that silane droplets had a diameter of less than 0.5 µm.

Comparative Example 2

A white aqueous emulsion was obtained in the same manner as in Example 1 except that the number of revolution of the homomixer was changed from 10,000 rpm to 2,000 rpm and that the stirring time with a homomixer was changed from 60 minutes to 10 minutes. The emulsion was observed through an optical microscope to show that silane droplets had diameters ranging from 5 µm to 50 µm.

The aqueous emulsions obtained in Examples 1 to 7 and Comparative Examples 1 and 2 were tested as follows. Table 1 shows the results.

(Measurement of depth of infiltration)

An emulsion sample was applied to a bottom face of a 7 cm×7 cm×2 cm mortar test piece (JIS R 5201) at a rate of 300 g/m$^2$. After 24 hours, the test piece was split into two. A 5% methylene blue aqueous solution was applied to a cross section of one split piece, a hydrophobic layer which was not stained was measured for thickness in five places, and the measurement values were averaged.

(Water absorption test)

An emulsion sample was applied to all the surfaces of a 7 cm×7 cm×2 cm mortar test piece (JIS R 5201) at a rate of 300 g/m$^2$, and dried at room temperature for 28 days. Then, the test piece was subjected to a water absorption test according to JIS A 1404, and the ratio of 24 hours' water absorption of the test piece to 24 hours' water absorption of a test piece to which no emulsion was applied was determined.

(Test on stability of emulsion)

50 Grams of an emulsion sample was placed in a 100 cc glass bottle, and the bottle was tightly closed. The bottle was allowed to stand at room temperature for 1.5 years and then the content was visually observed for an emulsion state (phase-separation state).

(Test on re-emulsification)

After the above test on stability of emulsion, the bottle was manually shaken 30 times, allowed to stand at room temperature for 1 hour and visually observed for an emulsification state (A:emulsified, B:not emulsified)

(Test on wet color)

After the above test on re-emulsification, the bottle was again manually shaken 30 times, and the content was applied to a bottom face of a mortar test piece at a rate of 300 g/m$^2$, and dried at room temperature for 7 days. The applied surface of the test piece was visually observed for a wet color.

TABLE 1

|  | Diameter of droplet (µm) | Depth of infiltration (mm) |
| --- | --- | --- |
| Ex. 1 | 2 | 4.3 |
| Ex. 2 | 5 | 4.6 |
| Ex. 3 | 8 | 4.5 |
| Ex. 4 | 5 | 4.7 |
| Ex. 5 | 1 | 4.0 |
| Ex. 6 | 5 | 4.3 |
| Ex. 7 | 5 | 4.0 |
| CEx. 1 | <0.5 | 4.4 |

TABLE 1-continued

| | | | |
|---|---|---|---|
| CEx. 2 | 5–50 | | 4.2 |

| | After storage at room temperature for 1.5 years | | | |
|---|---|---|---|---|
| | Water absorption ratio | State of phase separation | Re-emulsification | Wet color |
| Ex. 1 | 0.05 | White/colorless | A | No |
| Ex. 2 | 0.05 | White/colorless | A | No |
| Ex. 3 | 0.05 | White/colorless | A | No |
| Ex. 4 | 0.04 | White/colorless | A | No |
| Ex. 5 | 0.06 | white/colorless | A | Almost no |
| Ex. 6 | 0.05 | White/colorless | A | No |
| Ex. 7 | 0.05 | White/colorless | A | No |
| CEx. 1 | 0.26 | Colorless/opaque | B | Wet color |
| CEx. 2 | 0.05 | Colorless/semi-transparent | B | No |

The aqueous alkylalkoxysilane emulsion of the present invention shows a stable emulsion state for a long period of time, and is useful as a water-based infiltrative water-absorption preventer for porous inorganic construction materials such as concrete.

What is claimed is:

1. An aqueous alkylalkoxysilane emulsion comprising an alkylalkoxysilane, water and an emulsifier, wherein droplets of the alkylalkoxysilane in the water has a diameter in the range of 2 to 10 μm.

2. The emulsion according to claim 1, wherein the alkylalkoxysilane comprises at least one alkyl group having 6 to 20 carbon atoms, at least one alkoxy group having 1 to 3 carbon atoms and a silicon atom, the alkyl group and the alkoxy group bonding directly to the silicon atom.

3. The emulsion according to claim 2, wherein the alkylalkoxysilane is a monoalkyltrialkoxysilane.

4. The emulsion according to claim 1, wherein the alkylalkoxysilane has a concentration of 5 to 70% by weight in water.

5. The emulsion according to claim 1, wherein the emulsifier is contained in an amount of 0.1 to 50% by weight based on a silane component.

6. The emulsion according to claim 1, wherein the emulsifier is at least one member selected from the group consisting of an anionic emulsifier, a nonionic emulsifier, a cationic emulsifier and an amphoteric emulsifier.

7. The emulsion according to claim 6, wherein the emulsifier consists of a nonionic emulsifier and 0.01 to 20% by weight, based on the total weight of the emulsifier, of an anionic emulsifier.

8. A process for the production of an aqueous alkylalkoxysilane emulsion, which comprises emulsifying and dispersing an alkylalkoxysilane, water and an emulsifier under conditions sufficient to form an emulsion in which droplets of the alkylalkoxysilane in the water has a diameter in the range of from 2 to 10 μm.

9. The process according to claim 8, wherein the alkylalkoxysilane, the water and the emulsifier are emulsified and dispersed at a temperature which does not exceed 50° C.

10. An infiltrative water-absorption preventer for a porous inorganic construction material, which comprises the aqueous alkylalkoxysilane emulsion recited in claim 1 as an active ingredient.

11. The infiltrative water-absorption preventer according to claim 10, wherein the preventer further comprises at least one additive selected from the group consisting of a pH adjusting agent, an antiseptic agent, a mildew proofing agent, an antibacterial agent, a thickening agent, a water-based water repellency agent, an anti-foaming agent, an oil-soluble dye and a water-based colorant.

* * * * *